(12) United States Patent
Caron et al.

(10) Patent No.: US 6,489,334 B2
(45) Date of Patent: Dec. 3, 2002

(54) METHOD FOR THE CRYSTALLIZATION OF A TETRAHYDROPYRIDIN DERIVATIVE AND RESULTING CRYSTALLINE FORMS

(75) Inventors: Antoine Caron, Montbazin (FR); Bruno Franc, Saze (FR); Olivier Monnier, Villeveyrac (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/947,821

(22) Filed: Sep. 6, 2001

(65) Prior Publication Data

US 2002/0026057 A1 Feb. 28, 2002

Related U.S. Application Data

(63) Continuation of application No. 09/331,513, filed as application No. PCT/FR97/02393 on Dec. 23, 1997, now abandoned.

(30) Foreign Application Priority Data

Dec. 23, 1996 (FR) .............................................. 96 15904

(51) Int. Cl.[7] .................. A61K 31/4418; C07D 211/70; A61P 25/28
(52) U.S. Cl. ........................................ 514/277; 546/346
(58) Field of Search ........................... 514/277; 546/346

(56) References Cited

U.S. PATENT DOCUMENTS 4,521,428 A    6/1985    Nisato et al.

*Primary Examiner*—Evelyn Mei Huang
(74) *Attorney, Agent, or Firm*—Paul E. Dupont; Michael D. Alexander

(57) ABSTRACT

The invention relates to a method of crystallizing a tetrahydropyridine derivative, to the novel crystalline forms thereby obtained and to the pharmaceutical compositions containing said tetrahydropyridine derivative in a given crystalline form as the active principle.

31 Claims, 4 Drawing Sheets

METHOD FOR THE CRYSTALLIZATION OF A TETRAHYDROPYRIDIN DERIVATIVE AND RESULTING CRYSTALLINE FORMS

This application is a continuation of abandoned application Ser. No. 09/331,513 filed Jun. 22, 1999 as a 371 of PCT/FR97/02393 filed Dec. 23, 1997.

The present invention relates to a method of crystallizing a tetrahydropyridine derivative, to the novel crystalline forms thereby obtained and to a pharmaceutical composition containing said tetrahydropyridine derivative in a given crystalline form as the active principle.

The present invention relates more particularly to a method of crystallizing [-2-(2-naphthyl)ethyl]-4-(3-trifluoromethylphenyl)-1,2,3,6-tetrahydropyridine hydrochloride, to three crystalline forms of this product, to a defined mixture of two of these three forms and to a pharmaceutical composition containing one of said forms or a mixture of two of said forms.

1-[2-(2-Naphthyl)ethyl]-4-(3-trifluoromethylphenyl)-1,2,3,6-tetrahydropyridine, hereafter designated by its code number SR 57746, and its pharmaceutically acceptable salts were first described in EP 0 101 381 as anorexigenic agents and subsequently as antianxiodepressants (U.S. Pat. No. 5,026,716), anticonstipation agents (U.S. Pat. No. 5,109,005), neurotrophic agents (U.S. Pat. No. 5,270,320), free radical inhibitors (U.S. Pat. No. 5,292,745) and cardioprotective agents (U.S. Pat. No. 5,378,709).

EP 0 101 381 describes SR 57746 in the form of the hydrochloride, hereafter called SR 57746 A, and this salt was used in preclinical and clinical trials on healthy volunteers. According to said document, SR 57746 A is isolated by crystallization from ethanol, especially absolute ethanol.

In the preclinical trials, especially in the animal pharmacology and toxicology tests, SR 57746 A showed a constant activity and behavior. Likewise, the pharmacokinetic studies on animals gave constant and reproducible results.

By contrast, in the clinical trials carried out on healthy volunteers (Phase I), SR 57746 A was found to show a high variability in the plasma concentrations and the pharmacodynamic effects of the active principle.

In the first clinical trials on patients suffering from very serious diseases, especially amyotrophic lateral sclerosis, the dose of SR 57746 A was kept very low, namely 2 mg/day, at which dose the product proved promising (W. G. Bradley, paper entitled "New drugs for amyotrophic lateral sclerosis", American Academy of Neurology meeting, Mar. 23–30, 1996; pages 240-23/240-28).

It has furthermore been found that the preparation of larger amounts of SR 57746 A by the method of isolation described in EP 0 101 381 does not successfully yield a product with constant characteristics which makes it possible to overcome the disadvantages noted in the Phase I clinical trials.

It was found more particularly that, by the method of isolation described in EP 0 101 381, the SR 57746 A obtained consists of crystals whose size is not constant and specifically is greater than 150 micrometers; more particularly, it is 150–600 micrometers for at least about 75% of the crystals.

Moreover, it has been found that the SR 57746 A obtained by the method described in EP 0 101 381 consists of at least 3 different forms, as demonstrated by differential scanning calorimetry.

Finally, it has been found that the respective ratios of the different forms are not constant in different production lots of SR 57746 A, making it difficult to control the characteristics of the starting material for the manufacture of pharmaceutical compositions.

It has now been found that by carrying out the crystallization of SR 57746 A under suitable and constant conditions in terms of solvent, stirrer speed and cooling rate, it is possible to isolate the compound in three different crystalline forms or as a mixture of two of these three forms in fixed and reproducible ratios.

More particularly, it has been found that:
 form I of SR 57746 A is obtained by cooling a solution of SR 57746 A in an ethanol/concentrated hydrochloric acid mixture, without stirring;
 form II of SR 57746 A is obtained by cooling a solution of SR 57746 A in absolute ethanol or in an ethyl acetate/water mixture under controlled conditions of cooling rate and stirrer speed;
 form III of SR 57746 A is obtained by cooling a solution of SR 57746 A in dimethyl sulfoxide; and
 a mixture of form I and form III in fixed and reproducible proportions is obtained by cooling a solution of SR 57746 A in an ethanol/water mixture.

It has also been found that these novel crystalline forms, either by themselves or in fixed mixtures of two of said forms, are absorbed uniformly and reproducibly and make it easy to establish the optimum dosage of the active principle. Over and above the improvements in pharmacokinetic and pharmacodynamic terms, the ability to control the reproducibility of the composition of SR 57746 A in crystalline form is very advantageous as far as marketing of the drug is concerned.

Finally, it has been found that if the novel crystalline forms or the mixtures of two of said forms consist of very small crystals, especially micronized crystals, the activity of the active principle increases substantially and its absorption is uniform and constant, thus making it possible to administer small dosages with a very good therapeutic response and at the same time totally to control the potential side effects.

The attached Figures show the thermograms obtained by subjecting form I, form II, form III and a form I/form III mixture in a ratio of 65.7/34.3 to differential scanning calorimetry.

Figure 1:
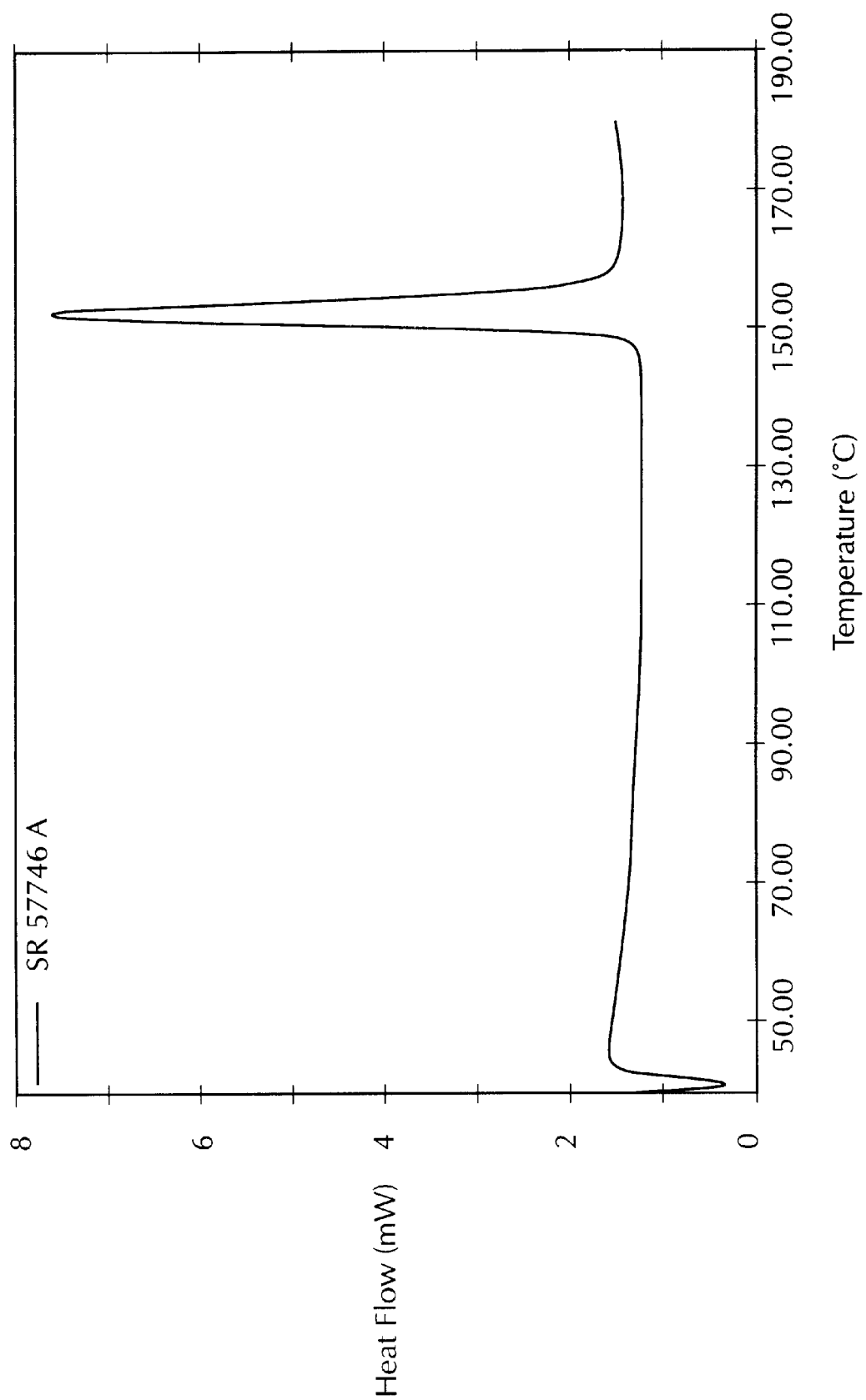
FIG. 1 shows the thermogram of form I of SR 57746 A, prepared according to Example 1, said thermogram being obtained by differential scanning calorimetry at 50° C. to 180° C. This thermogram shows a solid-solid transition temperature of 148–149° C.

Thus, according to one of its aspects, the present invention relates to a method of crystallizing 1-[2-(2-naphthyl)ethyl]-4-(3-trifluoromethylphenyl)-1,2,3,6-tetrahydropyridine hydrochloride, characterized in that:
 (a) said compound is dissolved by heating in a solvent selected from alkanols having 1 to 3 carbon atoms, ketones having 3 to 6 carbon atoms, dimethyl sulfoxide and ethyl acetate, said solvent optionally containing from 5 to 30% by volume of water or aqueous hydrochloric acid;

(b) the resulting solution is cooled to −10/+10° C. at a rate of 3 to 100° C./hour, with stirring at 0 to 600 rpm; and (c) the resulting product is isolated and optionally micronized.

The method of the present invention is carried out according to the conventional procedure of crystallization techniques, but the type of solvent, the cooling rate, the absence or presence of water and the stirrer speed constitute essential parameters for the reproducible preparation of one crystalline form rather than another or for the reproducible preparation of a mixture of two forms in fixed ratios.

In step (a), a 1-[2-(2-naphthyl)ethyl]-4-(3-trifluoromethylphenyl)-1,2,3,6-tetrahydropyridine hydrochloride, for example the crude product obtained by the method described in EP 0 101 381, is heated, preferably under reflux, in the chosen solvent, optionally in the presence of water.

The presence of water can prove useful for completely solubilizing the SR 57746 A. Thus, in methanol and ethanol, for example, the product dissolves completely at a reasonable concentration (for example 15–150 g/l), whereas it does not dissolve completely in acetone, methyl ethyl ketone, isopropanol or ethyl acetate at the same concentrations. In these solvents, it then suffices to add 5 to 30% of water in order to bring about complete solubilization at the reflux temperature. The percentage of water must not be too high, however, in order to avoid excessive solubilization and a loss of final product.

In one advantageous procedure, the solvent used is selected from the following mixtures (v/v): 100/0 to 70/30 methanol/water, 100/0 to 70/30 ethanol/water, 95/5 to 70/30 acetone/water, 95/5 to 80/20 methyl ethyl ketone/water and 95/5 to 70/30 ethyl acetate/water, and dimethyl sulfoxide.

As mentioned above, the concentration of the SR 57746 A in the chosen solvent depends on the solubility. It can range from about 15–100 g/l for ethyl acetate/water mixtures to 150–300 g/l for ethanol and ethanol/water mixtures.

The SR 57746 A is advantageously dissolved at a concentration of 5–150 g/l, preferably 100–150 g/l, in ethanol, an approximately 90/10 ethanol/water mixture or methanol, at about 60 g/l in an approximately 90/10 acetone/water mixture, at 100–125 g/l in an approximately 95/15 methyl ethyl ketone/water mixture or at about 15 g/l in an approximately 90/10 ethyl acetate/water mixture. Solubilization in the solvent under reflux is total under these conditions.

In step (b), the solution obtained is cooled, optionally with stirring; the cooling rate is monitored and, if a stirrer is used, the stirrer speed is monitored because the production of a suitable crystalline form depends to a large extent on these two parameters.

If the crystallization is carried out with stirring, it is preferable to use a paddle stirrer (also called an impeller stirrer hereafter) to enable all the liquid to be rotated, the diameter of rotation of said stirrer being between 4/5 and 2/5 that of the reactor used.

The cooling rate is regulated with a temperature gradient which can range from 100 to 3° C. per hour.

The production of a particular crystalline form, rather than a mixture of two forms in fixed proportions, depends on the above two parameters simultaneously, in a given solvent, it being understood that the stirrer speed generally varies as a direct function of the cooling rate.

In step (c), the product crystallized in this way is isolated by the conventional techniques and optionally micronized.

The isolation of the product may allow for example the drying of the compound obtained; it has been demonstrated that the drying step—be it carried out in an oven or in a stirred drier—does not modify the crystalline structures obtained at the end of the crystallization.

By choosing the appropriate conditions for steps (a) and (b), four different species of SR 57746 A, namely form I, form II, form III or a form I/III mixture, can be isolated in step (c), it being possible to determine the essential characteristics of said species by differential scanning calorimetry (DSC); by means of thermograms obtained with a PERKIN-ELMER calorimeter under well-defined conditions, this gives:

the solid-solid transition temperature; and the enthalpy associated with this transition.

The differential scanning calorimetry was performed using a PERKIN-ELMER DSC7 apparatus, which was calibrated relative to the fusion endotherms of indium or lead and cyclohexane. This analysis was carried out on 3 to 6 mg of product in an aluminum cup with a crimped and pierced lid, over the temperature range 50 to 180° C., at a heating rate of 10° C./minute, using nitrogen as the flush gas.

The solid-solid transition temperature and the enthalpy of transition constitute essential characteristics which are in themselves sufficient to identify each crystalline form or mixtures of two of said forms.

Said forms can also be characterized by X-ray powder diffractometry. The X-ray powder diffraction profile (Bragg diffraction angles 2 θ) was established using a SIEMENS 500 TT diffractometer with a 40 kV generator, rear monochromator, Cu k×1 source and silicon holder, over a scanning range of 4° to 40° at a rate of 1° per minute.

In one advantageous method, step (a) is carried out by refluxing the SR 57746 A in a 95/5 to 70/30 ethanol/hydrochloric acid mixture until dissolution is complete, and step (b) is carried out by cooling the resulting solution to about 4° C. with a temperature gradient of 3 to 100° C. per hour, without stirring. By this advantageous procedure, the crystalline form of SR 57746 A is isolated in step (c), called "form I" hereafter, and is characterized in that it has:

a solid-solid transition temperature of 148.4±1.6° C.; and an enthalpy of transition of 26.4±1.1 J/g.

Form I of SR 57746 A, having the above characteristics, constitutes a further aspect of the present invention.

This novel crystalline form was also analyzed by X-ray powder diffraction. A qualitative study of the diffraction patterns made it possible to establish that form I has characteristic lines (2 θ) at:

9.9±0.3°

14.8±0.3°

20.8±0.3° (intensity: 100).

Form I is also obtained if the solution in step (b) is cooled by being left to stand for 8–15 hours at 0–5° C., again without stirring.

In another advantageous procedure, step (a) is carried out by refluxing in absolute ethanol or a 95/5 to 75/15 ethyl acetate/water mixture until dissolution is complete, the SR 57746 A being present in this solution at a concentration of 10–80 g/l, preferably 70 g/l, in the ethyl acetate/water mixture or 5–150 g/l in absolute ethanol.

In this advantageous procedure, step (b) is carried out by cooling from the reflux temperature to about 5° C. with a temperature gradient of 100 to 30° C. per hour and a stirrer speed of 100 to 600 rpm.

Another crystalline form is thus isolated in step (c), called "form II" hereafter, which is characterized in that it has:

a solid-solid transition temperature of 153.9±1.1° C.; and an enthalpy of transition of 24.1±1.0 J/g.

Form II of SR 57746 A, having the above characteristics, constitutes a further aspect of the present invention.

This novel crystalline form was also analyzed by X-ray powder diffraction. A qualitative study of the diffraction patterns made it possible to establish that form II has characteristic lines (2 θ) at:

14.5±0.3°(intensity: 100)

19.3±0.3°

20.4±0.3°.

In another advantageous procedure, step (a) is carried out by refluxing the SR 57746 A in dimethyl sulfoxide until dissolution is complete, and step (b) is carried out by cooling the resulting solution with a temperature gradient of 3 to 100° C. per hour and a stirrer speed of 0 to 600 rpm.

Another crystalline form is thus isolated in step (c), called "form III" hereafter, which is characterized in that it has:

a solid-solid transition temperature of 141±2° C.; and an enthalpy of transition of 17.6±0.5 J/g.

Form III of SR 57746 A, having the above characteristics, constitutes a further aspect of the present invention.

In one particularly advantageous procedure, step (a) is carried out by heating the SR 57746 A in a 95/5 to 70/30, preferably 90/10 to 85/15, ethanol/water mixture until dissolution is complete, and step (b) is carried out by cooling with a temperature gradient of 5 to 30° C. per hour, advantageously to 5° C. with a temperature gradient of 10 to 20° C. per hour, preferably 10° C. per hour, and a stirrer speed of 0 to 600 rpm, advantageously 200 to 400 rpm and preferably 400 rpm.

Unexpectedly, it has been found that a form I/form III mixture in weight ratios of 80/20 to 60/40, advantageously 70/30 to 65/35 and preferably about 66/34, as demonstrated by differential scanning calorimetry, is isolated reproducibly in step (c).

This mixture is made up of particles with a diameter below 150 micrometers.

Forms I, II and III of SR 57746 A and the mixture of forms I and III can be micronized to give a pharmaceutical active principle with a particle size below 50 micrometers, advantageously below 30 micrometers and preferably, for at least 80% of the particles, below 10 micrometers.

The micronization can be carried out in a conventional apparatus for obtaining microcrystals with a size below 50 micrometers, for example in an ALPINE 200 AS micronizer, the SR 57746 A being introduced into the micronization chamber (diameter of 200 mm) at a rate of 15 to 50 kg/hour and a working pressure of 1 to 6.5 bar, and the product being recovered in a filter bag.

The micronized crystalline forms I, II and III of SR 57746 A and the micronized mixtures of forms I and III in ratios of 80/20 to 60/40, advantageously 70/30 to 65/35 and preferably about 66/34 constitute a particularly advantageous aspect of the present invention.

The availability of well-defined forms of SR 57746 A or a fixed form I/form III mixture makes it possible to prepare pharmaceutical compositions which have a constant and reproducible composition.

Furthermore, the preparation of a product which has a fine particle size, for example by micronization, makes it possible—for a constant activity—substantially to reduce the effective doses for obtaining the same therapeutic result.

More particularly, it has been demonstrated that the microcrystalline form not only makes it possible to reduce the dosage amount present in the pharmaceutical compositions, but also, in particular, makes it possible to render the oral absorption uniform and thus to have a constant therapeutic response in every patient, whether the product be administered on an empty stomach or with a meal.

A study concerning the determination of the in vitro absorption of SR 57746 A as a micronized form I/III mixture was carried out using the CACO-2 monolayer model. This test, which is widely used as a predictive intestinal epithelial model for drug absorption (P. Artusson, Crit. Rev. Ther. Drug, 1991, 8: 305–330), made it possible to show significant differences in terms of dissolution and permeability between SR 57746 A as a micronized form I/III mixture and the SR 57746 A obtained according to EP 0 101 381.

The results show that, in the medium used (Hanks' solution supplemented with 10% of fetal calf serum and taurocholic acid), the rates of dissolution and permeability are significantly different for SR 57746 A as a micronized form I/III mixture and for the SR 57746 A obtained according to EP 0 101 381. More particularly, it was demonstrated that the dissolution and permeability are normalized—i.e. rendered uniform—after micronization.

Thus, according to another of its aspects, the present invention relates to a pharmaceutical composition containing, as the active principle, 1-[2-(2-naphthyl)ethyl]-4-(3-trifluoromethylphenyl)-1,2,3,6-tetrahydropyridine hydrochloride in an optionally micronized, crystalline form selected from form I, form II and form III as defined above, and form I/form III mixtures in ratios of 80/20 to 60/40, advantageously 70/30 to 65/35 and preferably about 66/34.

The crystalline forms of the invention can conveniently be administered orally, parenterally, sublingually or transdermally. The amount of active principle to be administered depends on the nature and severity of the diseases to be treated and on the weight of the patients. Nevertheless, the amount of active principle present in the dosage unit can range up to 10 mg (calculated as the free base) for the non-micronized product and can be from 0.1 to 5 mg, advantageously from 0.5 to 3 mg and preferably 2 mg (calculated as the free base) for the micronized product. The preferred unit doses will generally comprise 0.5, 1, 1.5, 2, 2.5 or 3 mg (calculated as the free base) of micronized product.

These unit doses will normally be administered one or more times a day, for example once or twice a day, the overall dose in man varying between 0.5 and 20 mg per day, advantageously between 1 and 10 mg per day (calculated as the free base), for the non-micronized product and from 0.2 to 10 mg per day, advantageously between 1 and 6 mg per day (calculated as the free base), for the micronized product.

In the unit forms of the pharmaceutical compositions of the present invention, the active principle is administered to animals and humans, preferably as a mixture with conventional pharmaceutical carriers, for the treatment of the diseases indicated especially in patents U.S. Pat. No. 5,026,716, U.S. Pat. No. 5,109,005, U.S. Pat. No. 5,270,320, U.S. Pat. No. 5,292,745 and U.S. Pat. No. 5,378,709, and in particular for the treatment of neurodegeneration, especially amyotrophic lateral sclerosis. The appropriate unit forms of administration preferably include oral forms such as tablets, which may be divisible, gelatin capsules, powders and granules, and sublingual and buccal forms of administration, it also being possible for transdermal forms of administration to be prepared using the novel crystalline forms.

When preparing a solid composition in the form of tablets, the active principle is mixed with a pharmaceutical vehicle such as gelatin, starch, lactose, magnesium stearate, talcum, gum arabic or the like. The tablets can be coated with sucrose or other appropriate substances, or else they can be treated so as to have a prolonged or delayed activity and so as to release a predetermined amount of active principle continuously.

A preparation in the form of gelatin capsules is obtained by mixing the active ingredient with a diluent and pouring the resulting mixture into soft or hard gelatin capsules.

The active principle can also be formulated as microcapsules, optionally with one or more carriers or additives.

In the pharmaceutical compositions according to the present invention, the active principle can also be in the form of an inclusion complex in cyclodextrins, their ethers or their esters.

The following Examples illustrate the invention.

EXAMPLE 1

A mixture of 19.5 g of crude 1-[2-(2-naphthyl)ethyl]-4-(3-trifluoromethylphenyl)-1,2,3,6-tetrahydropyridine hydrochloride, 95 ml of absolute ethanol and 4.65 ml of 37% hydrochloric acid is refluxed, with stirring, until dissolution is complete and is then allowed to cool, with continued stirring. When the first crystals start to form (at about 63° C.), the stirrer is stopped and the reaction mixture is kept at 0–5° C. overnight. After filtration, the product is twice made into a paste in 30 ml of absolute ethanol and then dried overnight at 40° C. under vacuum.

Under these conditions, 12.8 g of form I of 1-[2-(2-naphthyl)ethyl]-4-(3-trifluoromethylphenyl)-1,2,3,6-tetrahydropyridine hydrochloride (SR 57746 A—form I) were obtained.

In differential scanning calorimetry, the SR 57746 A—form I obtained in this preparation had:

a solid-solid transition temperature of 148–149° C.; and an enthalpy of transition of 26.4 J/g.

The corresponding thermogram is shown in FIG. 1.

In X-ray powder diffraction analysis with a SIEMENS 500 TT diffractometer under the conditions given above, the SR 57746 A—form I obtained in this preparation has characteristic lines (Bragg angles 2 θ) at 9.8°, 14.7° and 20.7° (relative intensity: 100).

The X-ray powder diffraction profile (diffraction angles) of the SR 57746 A—form I of this preparation is given by the significant lines collated in Table 1, together with the relative intensity expressed as a percentage of the most intense line.

TABLE 1

| SR 57746 A - form I | |
|---|---|
| Diffraction bands (Bragg angles 2 θ) | Relative intensity |
| 9.798 | 23.44 |
| 14.758 | 79.68 |
| 15.174 | 45.73 |
| 16.584 | 49.31 |
| 16.922 | 34.30 |
| 17.458 | 35.91 |
| 17.814 | 21.48 |
| 18.403 | 32.33 |
| 20.741 | 100.00 |
| 21.367 | 29.91 |
| 22.310 | 28.98 |
| 24.482 | 22.75 |
| 24.768 | 67.67 |

TABLE 1-continued

| SR 57746 A - form I | |
|---|---|
| Diffraction bands (Bragg angles 2 θ) | Relative intensity |
| 25.644 | 40.18 |
| 28.803 | 39.03 |

EXAMPLE 2

In a METTLER RC1 calorimetric reactor equipped with an impeller stirrer of diameter 8 cm, a mixture of 70 g of crude 1-[2-(2-naphthyl)ethyl]-4-(3-trifluoromethylphenyl)-1,2,3,6-tetrahydropyridine hydrochloride and 1 l of absolute ethanol is refluxed until the product has completely dissolved. The resulting solution is cooled to 10° C. at a cooling rate of 80° C. per hour and a stirrer speed of 500 rpm. The resulting precipitate is filtered off and dried overnight at 45° C. under vacuum.

Under these conditions, form II of 1-[2-(2-naphthyl)ethyl]-4-(3-trifluoromethylphenyl)-1,2,3,6-tetrahydropyridine hydrochloride (SR 57746 A—form II) was obtained.

In differential scanning calorimetry, the SR 57746 A—form II obtained in this preparation had:

a solid-solid transition temperature of 153–155° C.; and an enthalpy of transition of 24.1 J/g.

Figure 2:
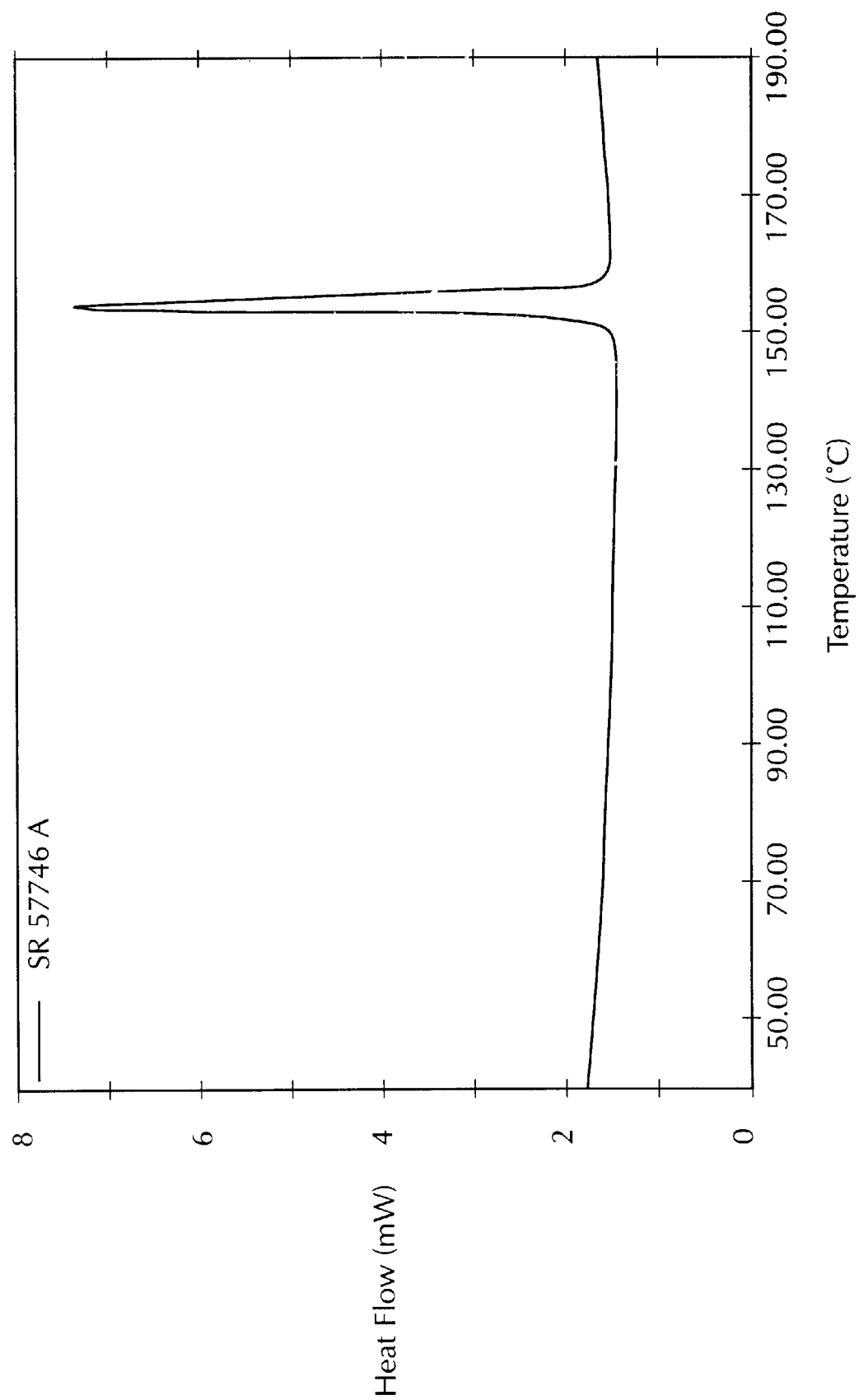
FIG. 2 shows the thermogram of form II of SR 57746 A, prepared according to Example 2, said thermogram being obtained by differential scanning calorimetry at 50° C. to 180° C. This thermogram shows a solid-solid transition temperature of 153–155° C.

The corresponding thermogram is shown in FIG. 2.

In X-ray powder diffraction analysis with a SIEMENS 500 TT diffractometer under the conditions given above, the SR 57746 A—form II obtained in this preparation has characteristic lines (Bragg angles 2 θ) at 14.3° (relative intensity: 100), 19.2° and 20.5°.

The X-ray powder diffraction profile (diffraction angles) of the SR 57746 A—form II of this preparation is given by the significant lines collated in Table 2, together with the relative intensity expressed as a percentage of the most intense line.

TABLE 2

| SR 57746 A - form II | |
|---|---|
| Diffraction bands (Bragg angles 2 θ) | Relative intensity |
| 14.348 | 100.00 |
| 16.300 | 21.68 |
| 16.748 | 57.51 |
| 17.209 | 68.98 |
| 19.173 | 34.10 |
| 20.147 | 37.38 |
| 20.493 | 28.52 |
| 20.832 | 33.62 |
| 24.332 | 37.28 |
| 24.902 | 24.57 |
| 25.237 | 41.71 |
| 25.817 | 24.57 |

EXAMPLE 3

A mixture of 2 g of crude 1-[2-(2-naphthyl)ethyl]-4-(3-trifluoromethylphenyl)-1,2,3,6-tetrahydropyridine hydrochloride and 50 ml of dimethyl sulfoxide is refluxed until dissolution is complete, the mixture is allowed to cool overnight and the crystalline product is then recovered and dried under vacuum at 45° C. overnight.

Under these conditions, form III of 1-[2-(2-naphthyl) ethyl]-4-(3-trifluoromethylphenyl)—1,2,3,6-tetrahydropyridine hydrochloride (SR 57746 A—form III) was obtained.

In differential scanning calorimetry, the SR 57746 A—form III obtained in this preparation had:

a solid-solid transition temperature of 141–142° C.; and an enthalpy of transition of 17.6 J/g.

Figure 3:
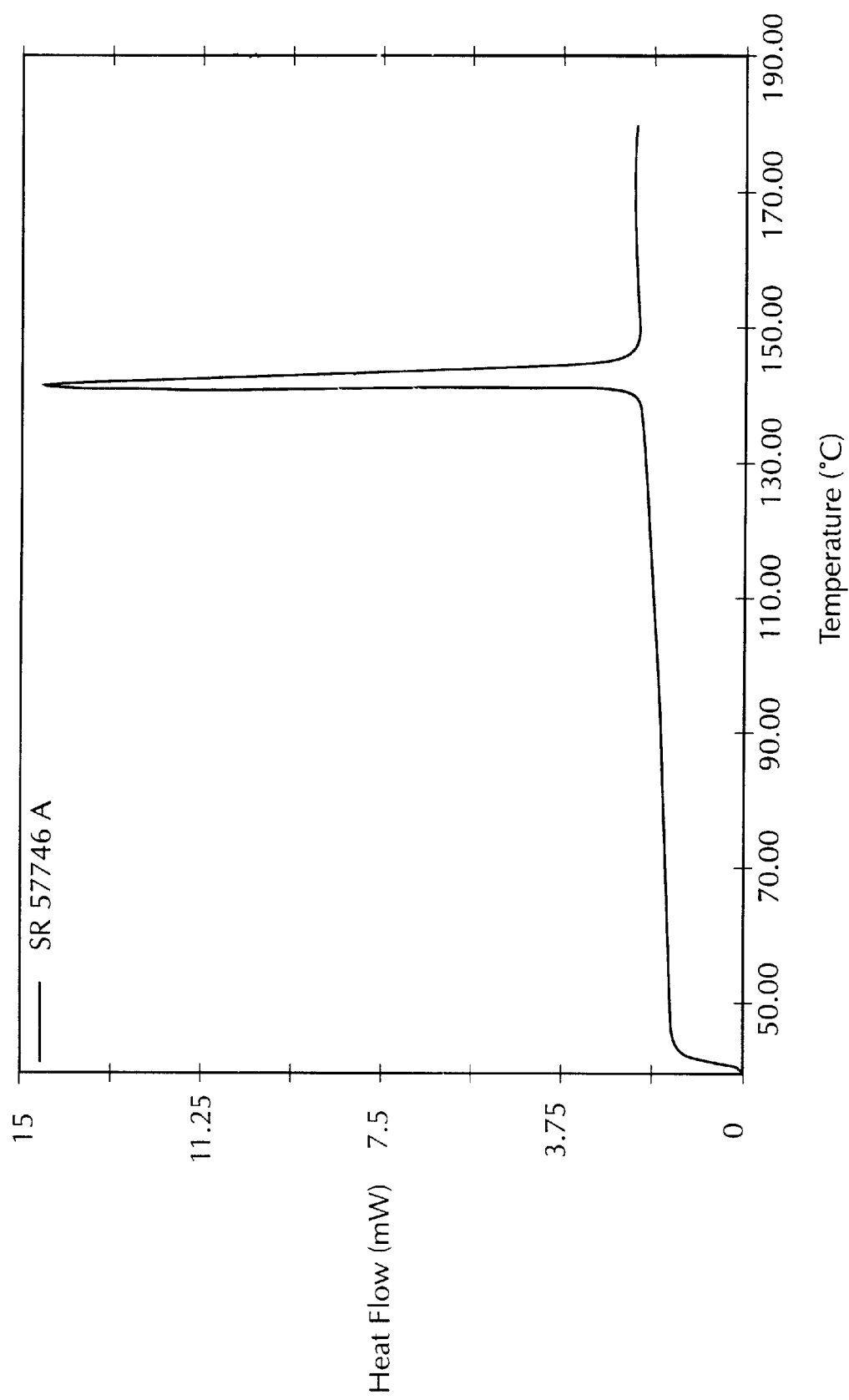
FIG. 3 shows the thermogram of form III of SR 57746 A, prepared according to Example 3, said thermogram being obtained by differential scanning calorimetry at 50° C. to 180° C. This thermogram shows a solid-solid transition temperature of 141–142° C.

The corresponding thermogram is shown in FIG. 3.

EXAMPLE 4

A mixture of 100 g of crude 1-[2-(2-naphthyl)ethyl]-4-(3-trifluoromethylphenyl)-1,2,3,6-tetrahydropyridine hydrochloride and 1 l of a 90/10 ethanol/water mixture is refluxed, with stirring, until the product has completely dissolved. The resulting solution is cooled from the reflux temperature to 5° C., with impeller stirring at 400 rpm, at a cooling rate of 10° C./hour. The resulting crystalline product is filtered off and dried at 45° C. under vacuum overnight.

Under these conditions, the 1-[2-(2-naphthyl)ethyl]-4-(3-trifluoromethylphenyl)-1,2,3,6-tetrahydropyridine hydrochloride was obtained as a form I/form III mixture in a ratio of 65.7/34.3 (SR 57746 A—form I/III).

Figure 4:
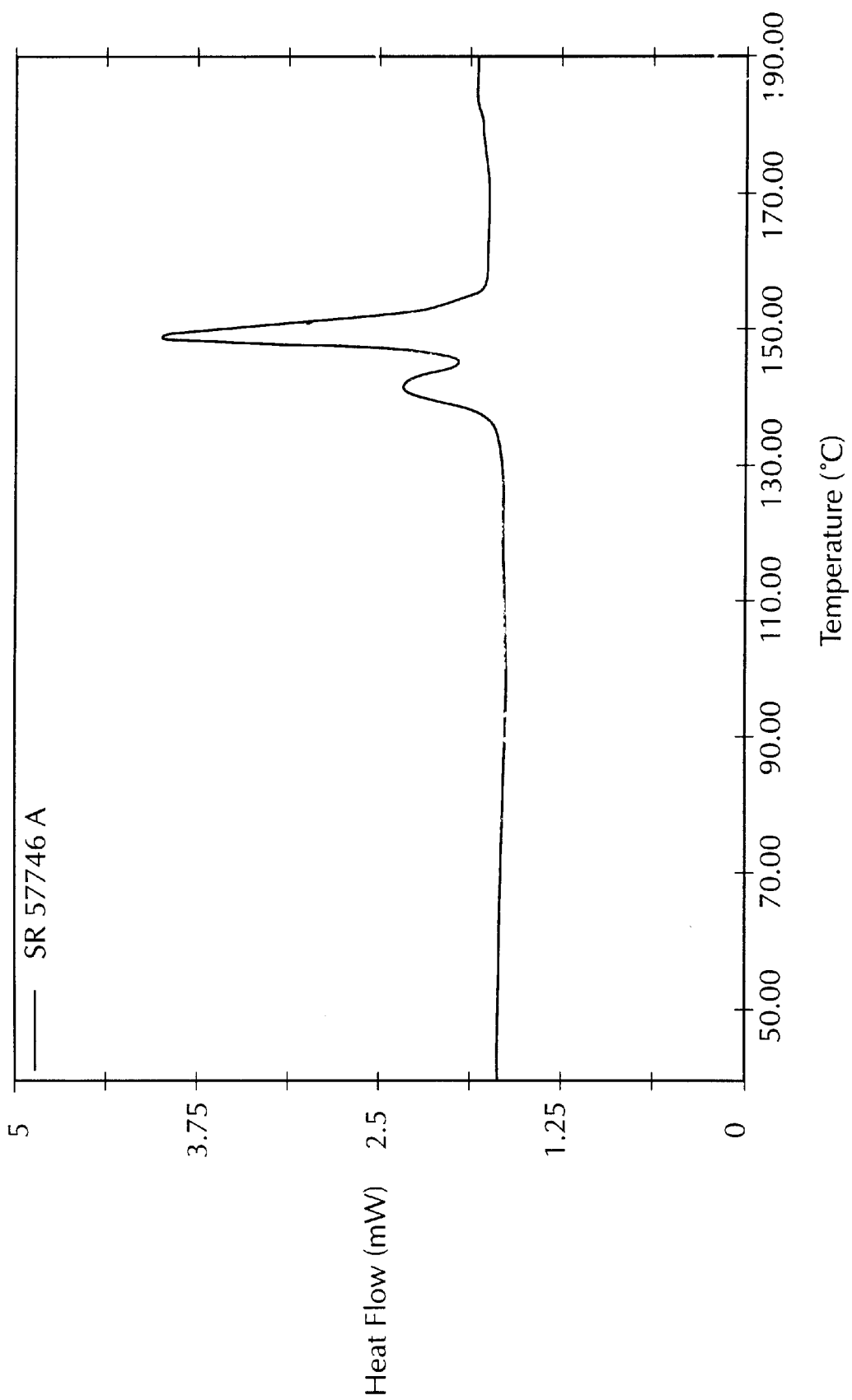
FIG. 4 shows the thermogram of a form I/form III mixture, prepared according to Example 4, said thermogram being obtained by differential scanning calorimetry at 50° C. to 180° C. This thermogram shows the solid-solid transition temperatures of the two forms.

In differential scanning calorimetry, the SR 57746 A—form I/III obtained in this preparation has a thermogram, shown in FIG. 4, which shows only the two characteristic peaks corresponding to forms I and III.

EXAMPLES 5 and 6

The procedure was as described in Example 2 and, in two different preparations, the cooling rate and stirrer speed were varied as follows:

cooling at 100° C./hour and stirring at 600 rpm (Ex. 5);

cooling at 30° C./hour and stirring at 300 rpm (Ex. 6).

Under these conditions, SR 57746 A—form II was obtained.

It has therefore been found that, when working in absolute ethanol at a concentration of 70 g/l, the production of form II depends on the cooling rate and the stirrer speed in accordance with a linear equation of the type y=ax+b.

For obtaining form II under these conditions, the equation is as follows:

$$R_{max}=4.23.V+170.51$$

in which $R_{max}$ is the stirrer speed in rpm and V is the cooling rate in ° C./hour. Consequently, to obtain form II, the stirrer speed must be less than or equal to $R_{max}$ for a given cooling rate.

EXAMPLE 7

A mixture of 15 g of crude 1-[2-(2-naphthyl)ethyl]-4-(3-trifluoromethylphenyl)-1,2,3,6-tetrahydropyridine hydrochloride and 1 of a 90/10 ethyl acetate/water mixture is refluxed until the product has completely dissolved, with stirring using an impeller stirrer of diameter 8 cm. The resulting solution is cooled to 5° C. at 60° C. per hour with a stirrer speed of 150 rpm and the resulting precipitate is then filtered off and dried under vacuum to give SR 57746 A—form II, which is identical to the product obtained according to Example 2.

EXAMPLES 8–11

In four different preparations, crude 1-[2-(2-naphthyl) ethyl]-4-(3-trifluoromethylphenyl)-1,2,3,6-tetrahydropyridine hydrochloride at a concentration of 70 g/l in a 92/8 ethyl acetate/water mixture (reaction volume: 1.3 l) is refluxed in an RC 1 reactor coupled with a PARTEC® 100 particle monitor from LASENTEC and equipped with an impeller stirrer of diameter 8 cm. After complete dissolution, the solution was cooled under the following conditions in the four preparations:

cooling at 100° C./hour and stirring at 400 rpm (Ex. 8);

cooling at 80° C./hour and stirring at 300 rpm (Ex. 9);

cooling at 50° C./hour and stirring at 200 rpm (Ex. 10);

cooling at 30° C./hour and stirring at 100 rpm (Ex. 11).

Under these conditions, SR 57746 A—form II was obtained.

It has been found that, when working in a 92/8 ethyl acetate/water mixture at a concentration of 70 g/l, the production of form II depends on the cooling rate and the stirrer speed in accordance with the following linear equation:

$$R_{max}=4.14.V-18.9$$

in which $R_{max}$ is the stirrer speed in rpm and V is the cooling rate in ° C./hour.

To obtain form II, the stirrer speed must therefore be less than or equal to $R_{max}$ for a given cooling rate.

EXAMPLE 12

Crude 1-[2-(2-naphthyl)ethyl]-4-(3-trifluoromethylphenyl)-1,2,3,6-tetrahydropyridine hydrochloride at a concentration of 60.6 g /l in a 90/10 acetone/water mixture is refluxed, with stirring, until dissolution is complete. The procedure described in Example 4 is then followed to give SR 57746 A—form I/III in a ratio of 80/20.

EXAMPLE 13

Crude 1-[2-(2-naphthyl)ethyl]-4-(3-trifluoromethylphenyl)-1,2,3,6-tetrahydropyridine hydrochloride at a concentration of 100 g/l in methanol is refluxed, with stirring, until dissolution is complete. The procedure described in Example 4 is then followed to give SR 57746 A—form I/III in a ratio of 80/20, which is identical to the product of Example 12.

EXAMPLE 14

Crude 1-[2-(2-naphthyl)ethyl]-4-(3-trifluoromethylphenyl)-1,2,3,6-tetrahydropyridine hydrochloride at a concentration of 100 g/l in a 70/30 ethanol/water mixture is refluxed, with stirring, until dissolution is complete. The procedure described in Example 4 is then followed to give SR 57746 A—form I/III in a ratio of 65.7/34.3, which is identical to the product of Example 4.

EXAMPLE 15

24 kg of SR 57746 A—form I/III, described in Example 4, are introduced into the micronization chamber (diameter 200 mm) of an ALPINE 200 AS micronizer at a rate of 25 kg/hour and at a working pressure of 6.5 bar and the thereby micronized product is recovered in a filter bag. This gives SR 57746 A—form I/III with a particle size distribution such that all the particles have a size below 20 micrometers and 85% of the particles have a size below 10 micrometers.

Differential scanning calorimetry of the resulting micronized product shows that the transition temperatures are not affected by micronization. Said transitions are of the solid-solid type. The SR 57746 A degrades before melting, which starts at 250° C.

EXAMPLE 16

Pharmaceutical composition containing, as the active principle, the SR 57746 A—form I/III (micronized) according to Example 15 above:

| | |
|---|---|
| Active principle | 2.192 mg |
| Corn starch | 141.218 mg |
| Anhydrous colloidal silica | 0.200 mg |
| Magnesium stearate | 0.400 mg |

The active principle is screened at 0.2 mm and then premixed with the excipients. This mixture is screened at 0.315 mm, remixed and then screened again at 0.315 mm. After a final mixing, the composition is introduced into no. 3 gelatin capsules at a rate of 170 mg of composition containing an amount of SR 57746 A—form I/III which corresponds to 2 mg of 1-[2-(2-naphthyl)ethyl]-4-(3-trifluoromethylphenyl)-1,2,3,6-tetrahydropyridine base.

What is claimed is:

1. Form I of 1-[2-(2-naphthyl)ethyl]-4-(3-trifluoromethylphenyl)-1,2,3,6-tetra-hydropyridine hydrochloride having
    a solid-solid transition temperature of 148.4±1.6° C.; and
    an enthalpy of transition of 26.4±1.1 J/g.

2. Form I of 1-[2-(2-naphthyl)ethyl]-4-(3-trifluoromethylphenyl)-1,2,3,6-tetra-hydropyridine hydrochloride, wherein its X-ray powder diffraction pattern has characteristic lines (Bragg angles 2 θ) at:
    9.9±0.3°
    14.8±0.3°
    20.8±0.3° (intensity:100).

3. Form II of 1[2-(2-naphthyl)ethyl]-4-(3-trifluoromethylphenyl)-1,2,3,6-tetra-hydropyridine hydrochloride having
    a solid-solid transition temperature of 153.9±1.1° C.; and
    an enthalpy of transition of 24.1±1.0 J/g.

4. Form II of 1-[2-(2-naphthyl)ethyl]-4-(3-trifluoromethylphenyl)-1,2,3,6-tetra-hydropyridine hydrochloride, wherein its X-ray powder diffraction pattern has characteristics lines (Bragg angles 2 θ) at:
    14.5±0.3° (intensity :100)
    19.3±0.3°
    20.4±0.3°.

5. Form III of 1-[2-(2-naphthyl)ethyl]-4-(3-trifluoromethylphenyl)-1,2,3,6-tetra-hydropyridine hydrochloride having
    a solid-solid transition temperature of 141±2° C.; and
    an enthalpy of transition of 17.6±0.5 J/g.

6. A mixture of form I and form III of 1-[2-(2-naphthyl)ethyl]-4-(3-trifluoromethylphenyl)-1,2,3,6-tetra-hydropyridine hydrochloride in a form I/form III ratio of 80/20 to 60/40, form I having an x-ray powder diffraction pattern with characteristic lines (Bragg angles 2 θ) at:
    9.9±0.3°
    14.8±0.3°
    20.8±0.3° (intensity:100),
and form III having
    a solid-solid transition temperature of 141±2° C.; and
    an enthalpy of transition of 17.6±0.5 J/g.

7. A method for preparing crystalline form I of 1-[2-(2-naphthyl)ethyl]-4-(3-trifluoromethylphenyl)-1,2,3,6-tetrahydropyridine hydrochloride according to claim 2 which comprises heating 1-[2-(2-naphthyl)ethyl]-4-(3-trifluoromethylphenyl)-1,2,3,6-tetrahydropyridine hydrochloride (SR 57746 A) in a 95/5 to 70/30 ethanol/hydrochloric acid mixture until dissolution is complete, cooling the resulting solution to about 4° C. with a temparature gradient of 3 to 100° C. per hour without stirring, and isolating the resulting crystalline form I.

8. A method for preparing crystalline form II of 1-[2-(2-naphthyl)ethyl]-4-(3-trifluoromethylphenyl)-1,2,3,6-tetrahydropyridine hydrochloride according to claim 4 which comprises heating 1-[2-(2-naphthyl)ethyl]-4-(3-trifluoromethylphenyl)-1,2,3,6-tetrahydropyridine hydrochloride (SR 57746 A) in absolute ethanol or a 95/5 to 75/15 ethyl acetate/water mixture until dissolution is complete, SR 57746 A being present in the solution at a concentration of 5–150 g/l in absolute ethanol or 10–80 g/l in the ethyl acetate/water mixture, cooling the resulting solution to about 5° C. with a temperature gradient of 100 to 30° C. per hour and a stirrer speed of 100 to 600 rpm, and isolating the resulting crystalline form II.

9. A method for preparing crystalline form III of 1-[2-(2-naphthyl)ethyl]-4-(3-trifluoromethylphenyl)-1,2,3,6-tetrahydropyridine hydrochloride according to claim 5 which comprises heating 1-[2-(2-naphthyl)ethyl]-4-(3-trifluoromethylphenyl)-1,2,3,6-tetrahydropyridine hydrochloride (SR 57746 A) in dimethyl sulfoxide until dissolution is complete, cooling the resulting solution with a temperature gradient of 3 to 100° C. per hour and a stirrer speed of 0 to 600 rpm, and isolating the resulting crystalline form III.

10. A method for preparing a mixture of crystalline forms I and III of 1[2-(2-naphthyl)ethyl]-4-(3-trifluoromethylphenyl)-1,2,3,6-tetrahydropyridine hydrochloride according to claim 6 which comprises heating 1-[2-(2-naphthyl)ethyl]-4-(3-trifluoromethylphenyl)-1,2,3,6-tetrahydropyridine hydrochloride (SR 57746 A) in a 95/5 to 70/30 ethanol/water mixture until dissolution is complete, cooling the resulting solution with a temperature gradient of 5 to 30° C. per hour and a stirrer speed of 0 to 600 rpm, and isolating the resulting crystalline form I/III mixture.

11. A method according to claim 10, wherein a 90/10 ethanol/water mixture is used and the resulting solution is cooled to 5° C. with a temperature gradient of 10 to 20° C. per hour and a stirrer speed of 200 to 400 rpm, to give a form I/III mixture of 1-[2-(2-naphthyl)ethyl]-4-(3-trifluoromethylphenyl)-1,2,3,6-tetrahydropyridine hydrochloride in a ratio of 70/30 to 65/35.

12. A method according to claim 11, wherein the temperature gradient is 10° C. per hour and the stirrer speed is 400 rpm, and a form I/III mixture of 1-[2-(2-naphthyl)ethyl]-4-(3-trifluoromethylphenyl)-1,2,3,6-tetrahydropyridine hydrochloride in a ratio of about 66/34 is isolated.

13. Form I of 1-[2-(2-naphthyl)ethyl]-4-(3-trifluoromethylphenyl)-1,2,3,6-tetrahydropyridine hydrochloride obtainable by the method of claim 7.

14. Form II of 1-[2-(2-naphthyl)ethyl]-4-(3-trifluoromethylphenyl)-1,2,3,6-tetrahydropyridine hydrochloride obtainable by the method of claim 8.

15. Form III of 1-[2-(2-naphthyl)ethyl]-4-(3-trifluoromethylphenyl)-1,2,3,6-tetrahydropyridine hydrochloride obtainable by the method of claim 9.

16. A mixture of form I and form III of 1-[2-(2-naphthyl)ethyl]-4-(3-trifluoromethylphenyl)-1,2,3,6-tetrahydropyridine hydrochloride obtainable by the method of claim 10.

17. A mixture according to claim 6 in a form I/form III ratio of 70/30 to 65/35.

18. A mixture according to claim 17 in a form I/form III ratio of about 66/34.

19. A mixture according to claim 6 wherein it is micronized.

20. A solid pharmaceutical composition containing, as the active principle 1[2-(2-naphthyl)ethyl]-4-(3-trifluoromethylphenyl)-1,2,3,6-tetrahydropyridine hydrochloride in which the active principle is a mixture according to claim 19, in the form of a dosage unit.

21. A composition according to claim 20, wherein each dosage unit contains an amount of micronized active principle which corresponds to a dose selected from 0.5, 1, 1.5, 2, 2.5 and 3 mg of free base.

22. A mixture of form I and form III of 1-[2-(2-naphthyl)ethyl]-4-(3-trifluoromethylphenyl)-1,2,3,6-tetrahydropyridine hydrochloride obtainable by the method of claim 11.

23. A mixture of form I and form III of 1-[2-(2-naphthyl)ethyl]-4-(3-trifluoromethylphenyl)-1,2,3,6-tetrahydropyridine hydrochloride obtainable by the method of claim 12.

24. A crystalline form according to any one of claims 1, 3 or 5 wherein it is micronized.

25. A solid pharmaceutical composition containing, as the active principle, 1-[2-(2-naphthyl)ethyl]-4-(trifluoromethylphenyl)-1,2,3,6-tetrahydropyridine hydrochloride in an optionally micronized, crystalline form selected from form I, form II, form III and form I/form III mixtures according to claim 6.

26. A method for the treatment of neurodegeneration which comprises administering to a patient in need of such treatment an effective amount of an active principle according to claim 24.

27. A method for the treatment of neurodegeneration which comprises administering to a patient in need of such treatment an effective amount of an active principle according to claim 6.

28. A method for the treatment of neurodegeneration which comprises administering to a patient in need of such treatment an effective amount of an active principle according to claim 19.

29. A solid pharmaceutical composition containing, as the active principle, 1-[2-(2-naphthyl)ethyl]-4-(3-trifluoromethylphenyl)-1,2,3,6-tetrahydropyridine hydrochloride in an optionally micronized, crystalline form selected from form I, form II, form III and form I/form III mixtures according to claim 24.

30. A solid pharmaceutical composition containing, as the active principle, 1[2-(2-naphthyl)ethyl]-4-(3-trifluoromethylphenyl)-1,2,3,6-tetrahydropyridine hydrochloride in an optionally micronized, crystalline form selected from form I, form II, form III and form I/form III mixtures according to one of claims 1 to 5 or 13 to 16.

31. A method for the treatment of neurodegeneration which comprises administering to a patient in need of such treatment an effective amount of an active principle according to any one of claims 1 to 5 or 13 to 16.

\* \* \* \* \*

UNITED STATES PATENT AND TRADEMARK OFFICE
CERTIFICATE OF CORRECTION

PATENT NO. : 6,489,334 B2
DATED : December 3, 2002
INVENTOR(S) : Caron et al.

It is certified that error appears in the above-identified patent and that said Letters Patent is hereby corrected as shown below:

Column 1,
Lines 14-15, "[-2-(2-naphthyl)ethyl]-4-(3-trifluoromethylphenyl)-1,2,3,6-tetrahydropyridine" should read -- 1-[-2-(2-naphthyl)ethyl]-4-(3-trifluoromethylphenyl)-1,2,3,6-tetrahydropyridine --

Column 9,
Line 56, "1 of 90/10" should read -- 11 of 90/10 --

Column 12,
Lines 32-33: "1[-2-(2-naphthyl)ethyl]-4-(3-trifluoromethylphenyl)-1,2,3,6-tetrahydropyridine" should read -- 1-[-2-(2-naphthyl)ethyl]-4-(3-trifluoromethylphenyl)-1,2,3,6-tetrahydropyridine --

Signed and Sealed this

Fifteenth Day of July, 2003

JAMES E. ROGAN
*Director of the United States Patent and Trademark Office*